(12) United States Patent
Haensler et al.

(10) Patent No.: US 6,780,421 B1
(45) Date of Patent: Aug. 24, 2004

(54) ADJUVANT FOR A VACCINE COMPOSITION

(75) Inventors: Jean Haensler, St. Genis-les-Ollières (FR); Emmanuelle Trannoy, Lyons (FR); Jorge Ronco, Lyons (FR)

(73) Assignee: Aventis Pasteur SA, Lyons (FR)

( * ) Notice: Subject to any disclaimer, the term of this patent is extended or adjusted under 35 U.S.C. 154(b) by 0 days.

(21) Appl. No.: 08/836,576

(22) PCT Filed: Nov. 14, 1995

(86) PCT No.: PCT/FR95/01495

§ 371 (c)(1),
(2), (4) Date: Sep. 9, 1997

(87) PCT Pub. No.: WO96/14831

PCT Pub. Date: May 23, 1996

(51) Int. Cl.$^7$ ............... A61K 45/00; A61K 38/00; A61K 39/00; A61K 39/145

(52) U.S. Cl. ............... 424/283.1; 514/2; 424/184.1; 424/210.1

(58) Field of Search ............... 424/278.1, 283.1, 424/209.1, 210.1, 184.1, 450; 514/2, 7, 44, 170, 529; 435/69.3, 455, 458

(56) References Cited

U.S. PATENT DOCUMENTS

| | | | |
|---|---|---|---|
| 4,053,585 A | * 10/1977 | Allison et al. | ............... 424/450 |
| 4,261,975 A | 4/1981 | Fullerton et al. | ............... 424/89 |
| 4,971,803 A | 11/1990 | Li et al. | ............... 424/450 |
| 5,100,662 A | 3/1992 | Bolcsak et al. | ............... 424/88 |
| 5,283,185 A | * 2/1994 | Epand et al. | ............... 435/172.3 |
| 6,124,270 A | * 9/2000 | Haensler | ............... 514/44 |

FOREIGN PATENT DOCUMENTS

| | | |
|---|---|---|
| EP | 0 356 339 A1 | 2/1990 |
| WO | WO 93/05162 | 3/1993 |
| WO | WO 93/14744 | 8/1993 |

OTHER PUBLICATIONS

Database SciSearch on Dialog, No. 09561750, Gregoriadis, Pharm Res 15(5):661–670, May 1998.*
Database SciSearch on Dialog, No. 06948805, Couper et al., Human Immunology, 59/8:493–499, Aug. 1998.*
Hui, K.M. et al., "Induction of alloreactive cytotoxic T Lymphocytes by intra–splenic immunization with allogeneic class I Major Histocompatibility Complex DNA and DC–chol cationic Liposomes," *J. Liposome Res.* 4(3):1075–1090 (Nov. 1994).

Gao, X. and Huang, L., "A Novel Cationic Liposome Reagent for Efficient Transfection of Mammalian Cells," *Biochem. Biophys. Res. Comm.* 179(1):280–285 (1991).
Gupta, R.K. et al., "Adjuvants —a balance between toxicity and adjuvanticity," *Vaccine* 11(3):293–306 (Apr. 1993).
Zhou, X. and Huang, L., "DNA transfection mediated by cationic Liposomes containing Lipopolylysine: characterization and mechanism of action," *Biochim. Biophys. Acta* 1189(2):195–203 (Jan. 1994).
Barnes, P. F. et al., "Patterns of Cytokine Production by Mycobacterium–Reactive Human T–Cell Clones," *Infect. Immun.* 61:197–203 (Jan. 1993).
Del Prete, G. et al., "The Role of T..1 and T..2 Subsets in Human Infectious Diseases," *Trends in Microbiol.* 2: 4–6 (Jan. 1994).
Ghalib, H. et al., "IL–12 Enhances Th1–Type Responses in Human *Leishmania donovani*Infections," *J. Immun.* 154:4623–4629 (May 1995).
Katsikis, P. et al., "Are CD4 $T_h1$ Cells Pro–inflammatory or anti–inflamatory? The Ratio of IL–10 to IFN–, or IL–2 Determines Their Function," *Intl. Immun.* 7:1287–1294 (Aug. 1995).
Li, S. et al., "DC–Chol Lipid System in Gene Transfer," *J. Controlled Release* 39:373–381 (1996).
Romagnani, S., "Biology of Human $T_H1$ and $T_H2$ Cells," *J. Clin. Immun.* 15:121–129 (Mar. 1995).
Sieling, P. and Modlin, R., "Cytokine Patterns at the Site of Mycobacterial Infection," *Immunobiol.* 191:378–387 (Oct. 1994).
Kersten and Crommelin. *Biochim. Biophys. Acta* (1995) 1241:117–138.
Tyrrell, et al. *Biochimica et Biophysica Acta* (1976) 457:257–302.
Haan, et al. *J. Liposomal Res.* (2000) 10:159–177.

* cited by examiner

*Primary Examiner*—James Housel
*Assistant Examiner*—Zachariah Lucas
(74) *Attorney, Agent, or Firm*—McDonnell Boehnen Hulbert & Berghoff LLP (57) ABSTRACT

An amphipathic compound including a sterol-derived lipophilic grouping bound to a cationic grouping for use as an adjuvant in the delivery of a vaccine composition. In a particular embodiment, the lipophilic grouping is a cholesterol derivative and the cationic grouping is a quaternary ammonium or a protonatable amine. A vaccine composition including one or more antigens with at least one amphipathic compound having a sterol-derived lipophilic grouping bound to a cationic grouping, is also disclosed.

25 Claims, 13 Drawing Sheets

ELISA IgG titre

FIGURE 14

ELISA IgA titre

Table 1

FIGURE 17

Table 2

FIGURE 18

ADJUVANT FOR A VACCINE COMPOSITION

The present application is the U.S. national phase of International Patent Application No. PCT/FR95/01495, for which the international filing date is Nov. 14, 1995.

The present invention relates to the field of vaccine compositions. More especially, the invention relates to new adjuvants used for increasing the immunogenicity of vaccine compositions.

There are a large number of antigens which, when injected into animals, will cause a production of antibodies which are specific to them. One of the principles of vaccination is to stimulate antibody production by the body of a man or an animal by administering chosen antigens thereto. The antibodies thus produced will then enable the body to defend itself against a subsequent infection. However, some antigens do not bring about sufficient stimulation of the immune system when they are administered alone. Hence an adjuvant which will enable the body's immune response to be increased has to be added to them in order to obtain a sufficient amount of antibody to be protective.

Among known adjuvants, aluminium hydroxide and aluminium phosphate, which are customarily used in human vaccines, may be mentioned. However, these compounds do not possess an adjuvant property with respect to all antigens. In particular, they do not enable the immunogenicity of influenza vaccine to be increased.

There is hence a need to be able to have adjuvants at one's disposal which enable the immunogenicity of the antigens administered in a vaccine composition to be increased, without any risk of toxicity.

In addition, it is advantageous to have adjuvants at one's disposal which are capable of inducing an immune response that manifests itself in a production of secretory antibodies, such as IgAs.

To this end, the invention provides for the use of an amphipathic compound comprising a lipophilic group derived from a sterol linked to a cationic group, for the production of a vaccine composition.

A subject of the invention is also the use of such an amphipathic compound as adjuvant in the administration of a vaccine.

A subject of the invention is also a vaccine composition comprising at least one antigen, characterized in that it comprises, in addition, at least one amphipathic compound possessing a lipophilic group derived from a sterol linked to a cationic group.

A further subject of the invention is a product containing at least one antigen and one amphipathic compound comprising a lipophilic group derived from a sterol linked to a cationic group, as a combination product for use simultaneously, separately or staggered over time in vaccination.

Another subject of the invention is a method for inducing an immune response in a mammal, consisting in administering at least one antigen to the mammal, characterized in that it consists in administering, in addition, at least one amphipathic compound comprising a lipophilic group derived from a sterol linked to a cationic group.

For the purposes of the present invention, the term amphipathic denotes a compound which possesses both a hydrophobic portion and a hydrophilic portion.

Among sterol derivatives capable of yielding the compounds according to the invention, cholesterol, phytosterol and ergosterol may be mentioned. Cholesterol derivatives are especially suitable.

The cationic group of the amphipathic compounds according to the invention can consist of a quaternary ammonium or an amine which can be protonated.

The lipophilic group is attached to the cationic group by means of an ester, ether, amide or carbamoyl link, among which ester, amide and carbamoyl links have the advantage that they can be hydrolysed in the cell.

The linkage between the 2 groups is preferably effected via a spacer arm consisting of a branched or unbranched alkyl chain comprising from 1 to 20 carbon atoms.

Among the compounds suitable for the purposes of the invention, there may be mentioned those mentioned in U.S. Pat. No. 5,283,185 and, in particular:

cholesteryl-3β-carboxamidoethylenetrimethyl-ammonium iodide, cholesteryl-3β-carboxamidoethylenamine, cholesteryl-3β-oxysuccinamidoethylene-trimethylammonium iodide, 3β-[N-(N',N'-dimethylaminoethane)carbamoyl]-cholesterol, 3β-[N-(polyethylenimine)carbamoyl]cholesterol among which 3β-[N-(N',N'-dimethylaminoethane)carbamoyl] cholesterol is especially advantageous.

The amphipathic compounds according to the invention may be obtained by condensation between a sterol derivative and a compound containing a cationic group, according to one of the methods described in "Advanced Organic Chemistry" Part B: Reactions and Synthesis (F. A. Carey and R. J. Sundberg—Plenum Publishing Corp.). More especially, some of the compounds according to the invention may be prepared according to the methods described in U.S. Pat. No. 5,283,185.

The amphipathic compounds obtained in alcoholic solution can then be dispersed in water or in an aqueous buffer, and can yield a suspension of micelles or of liposomes. Advantageously, the amphipathic compounds of the invention are combined with a neutral lipid such as a phospholipid, for example dioleoylphosphatidylethanolamine (DOPE) or dioleoylphosphatidylcholine (DOPC). This combination causes the amphipathic compounds according to the invention to organize themselves in the form of liposomes rather than micelles during the phase of dispersion in an aqueous environment. The molar proportion of neutral lipid combined with the amphipathic compounds is preferably greater than 20%.

The products obtained according to the invention did not give rise to any acute toxicity reaction when they were inoculated into mice.

The antigen used to induce a protective immune response consists of any antigen customarily used in a vaccine composition, either alone or in combination with another antigen.

In particular, the amphipathic compounds according to the invention prove to be good immunoadjuvants when they are combined with the influenza virus vaccine comprising, in particular: the HA protein which is a haemagglutinin located at the surface of the influenza virus envelope, the NP protein which is a capsid nucleoprotein linked to the viral RNA and an M protein or protein "matrix" of the envelope.

Combination between the antigen whose immunogenicity it is desired to increase and the micellar or liposomal suspension of amphipathic compounds takes place spontaneously by hydrophobic and electrostatic interaction on mixing the constituents.

The vaccine compositions obtained possess good stability. However, the liposomal suspension appears preferable to the micellar suspension.

In addition, the liposomal suspension can be sterilized by filtration and lyophilized.

It is obvious that it is possible to add ingredients traditionally used in vaccines, such as water, physiological saline or a buffer substance, to the vaccine compositions obtained.

Administration of the vaccine compositions obtained according to the invention may be performed by all the routes customarily used for the administration of vaccines, and in particular by the subcutaneous or intranasal route. It is also possible to choose a different route for the primary immunization and the booster immunization.

It is possible to administer separately the composition comprising the antigen and the composition containing the amphipathic compounds according to the invention; however, the administration of a liposomal composition of amphipathic compounds according to the invention combined with the antigen makes it possible not only to increase the humoral type immune response, but also to induce specific cytotoxic T lymphocytes.

A better understanding of the invention will be gained on reading the non-limiting examples which follow, reference being made to the figures.

EXAMPLE 1

Synthesis of 3β-[N-(N',N'-dimethylaminoethane)-carbamoyl]cholesterol (DC chol)

Figure 1:
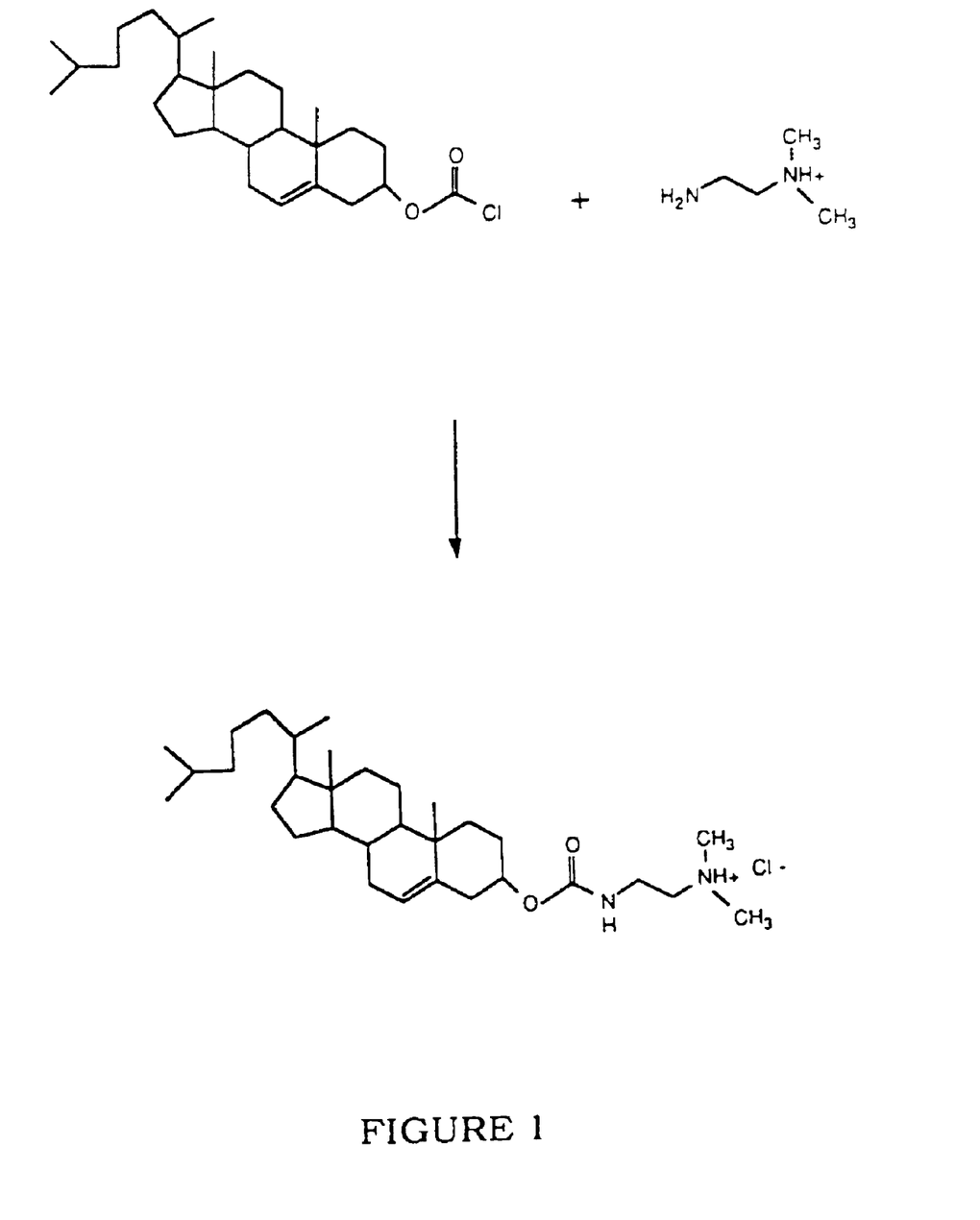
FIG. 1 illustrates the reaction scheme for the production of DC chol.
Figure 2:
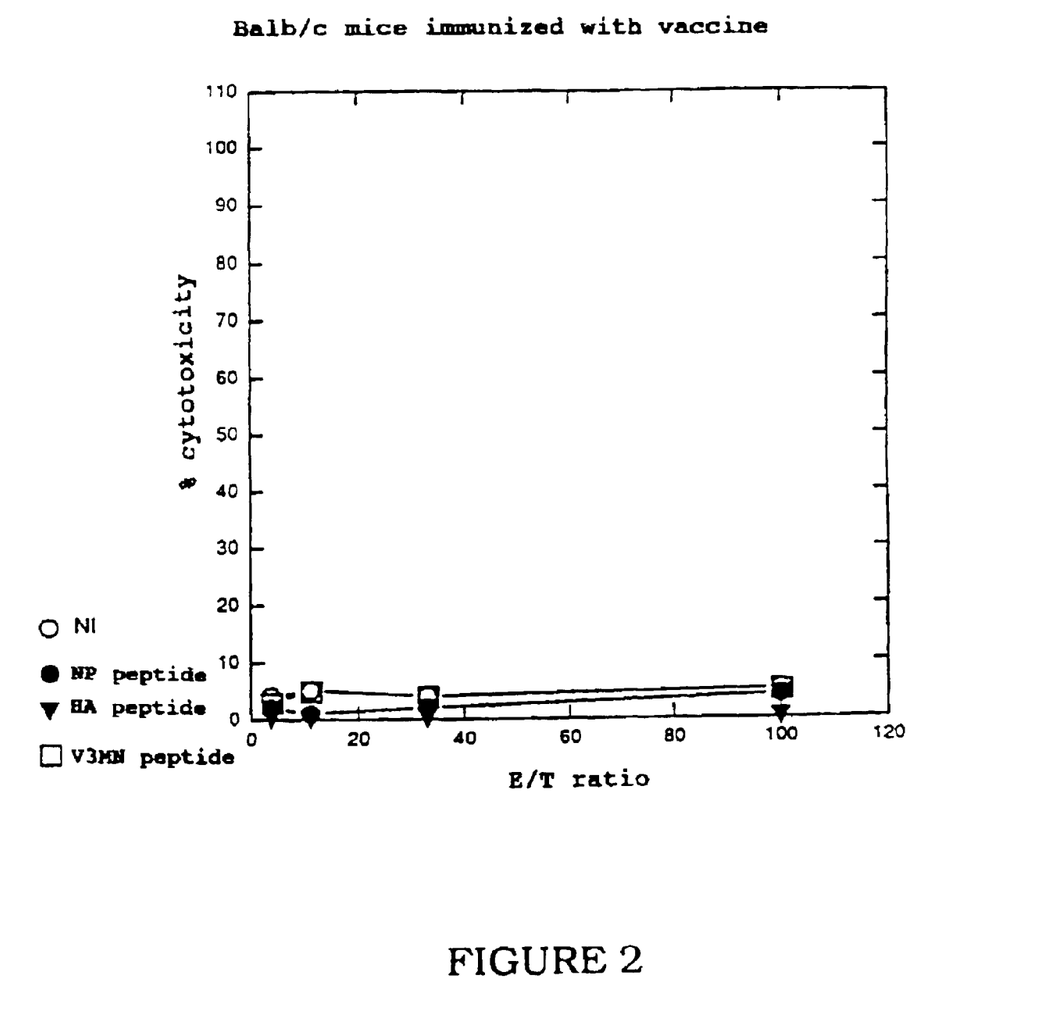
FIGS. 2 to 6 depict the results of tests of induction of cytotoxic T lymphocytes for each group of mice mentioned in Example 8.
Figure 3:
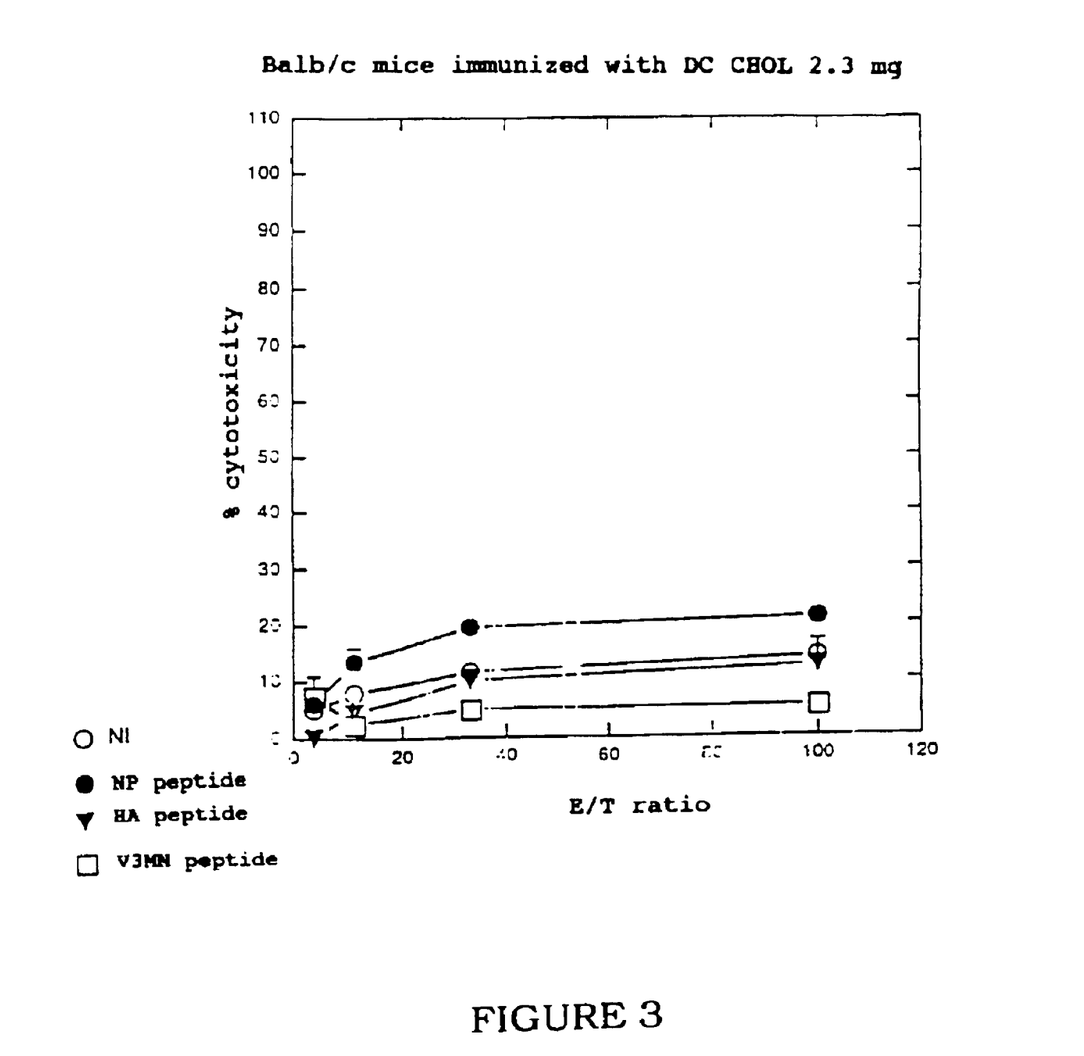
Figure 4:
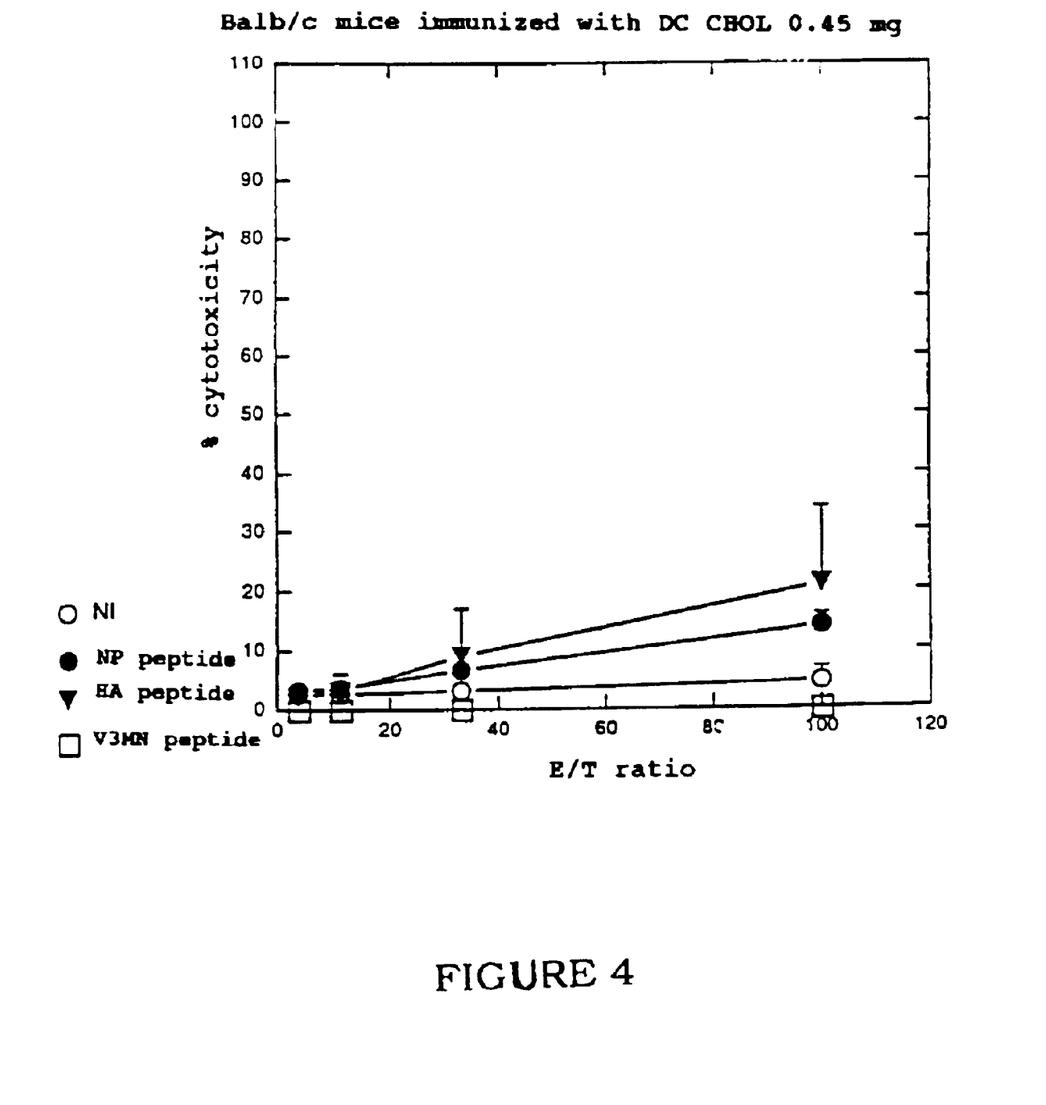
Figure 5:
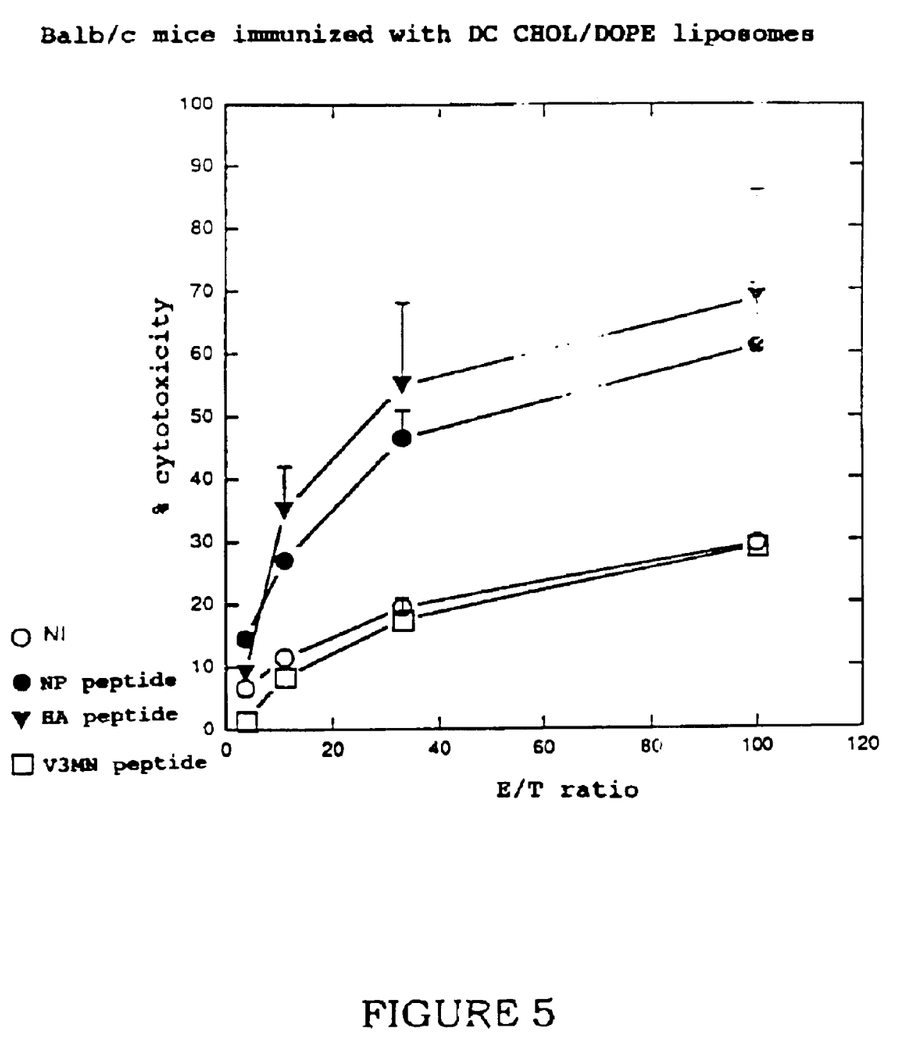
Figure 6:
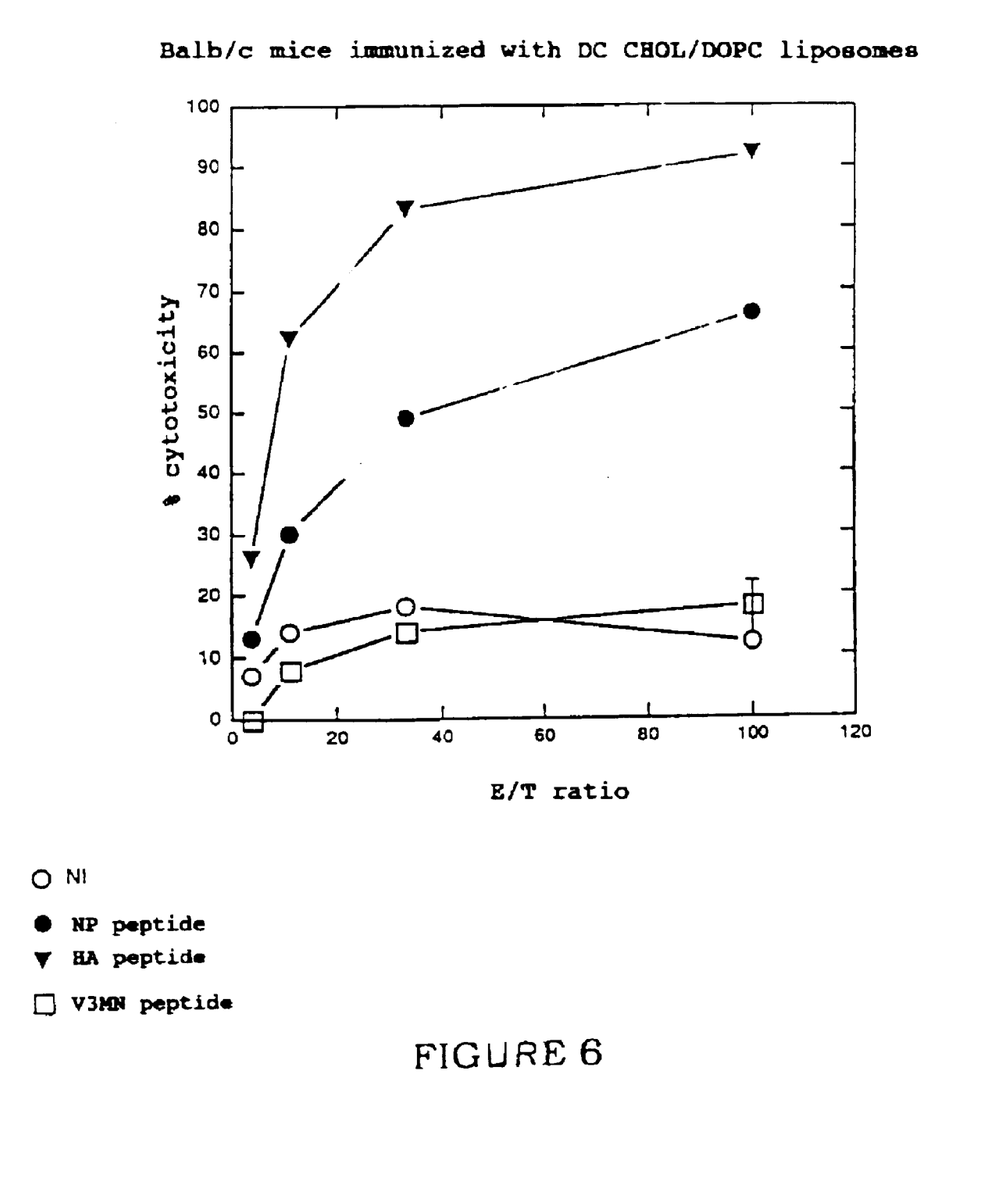

DC chol is synthesized by reacting cholesteryl chloroformate and N,N-dimethylethylenediamine according to the scheme in FIG. 1, as described in the paper by X. Gao and L. Huang (BBRC 179 (1): 280–285).

A solution of cholesteryl chloroformate (2.25 g, 5 mmol in 5 ml of dry chloroform) is added dropwise to an excess of a solution of N,N-dimethylethylenediamine (2 ml, 18.2 mmol, in 3 ml of dry chloroform) at 0° C. After extraction of the solvent by evaporation, the residue is purified by 2 successive recrystallizations in absolute ethanol at 4° C., and dried under vacuum. 0.545 g of DC chol is thereby obtained in the form of a white powder. The structure of the compound was verified by NMR and mass spectrometry. The results obtained are in agreement with the data published in the paper cited above.

EXAMPLE 2

Preparation of a Vaccine Composition Against Influenza Virus from a Micellar Suspension of DC chol 2.3 mg 30 mg of DC chol obtained according to Example 1 are dissolved in 100 μl of ethanol. 75 μl of the solution thereby obtained are injected via a Hamilton syringe into 3 ml of water kept stirring at 45° C. After a further 5 minutes of stirring at 45° C., the micellar suspension obtained is mixed with 200 μl of monovalent vaccine against influenza virus (Strain A/Singapore) comprising, in particular, as antigens: the haemagglutinin HA, nucleoprotein NP and M protein.

The mixture obtained is divided into vaccine doses of 0.3 ml. Each dose comprises 5 μg of HA and 2.3 mg of DC chol.

EXAMPLE 3

Preparation of a Vaccine Composition Against Influenza Virus from a Micellar suspension of DC chol 0.45 mg The procedure is as in Example 2, starting from 6 mg of DC chol obtained according to Example 1.

EXAMPLE 4

Preparation of a Suspension of Liposomes Consisting of DC chol Combined with Dioleoylphosphatidylethanolamine (DOPE)

18 mg of dioleoylphosphatidylethanolamine (DOPE) and 4.5 mg of DC chol obtained according to Example 1, which is dissolved in 3 ml of chloroform, are mixed.

The chloroform is evaporated off under vacuum to form a lipid film, which is subjected to dessication under vacuum and then resuspended in 3 ml of water.

After hydration for 24 hours at 4° C., the dispersion is subjected to sonication for 5 to 10 minutes in an ultrasound bath (Laboratory Supplies—Hicksville—N.Y.) to form liposomes.

This suspension is stable for at least 6 months at 4° C.

EXAMPLE 5

Preparation of a Suspension of Liposomes Consisting of DC chol Combined with Dioleoylphosphatidylcholine (DOPC)

The procedure is as in Example 4, replacing the 18 mg of DOPE by 18 mg of dioleoylphosphatidylcholine (DOPC).

A liposomal suspension which is stable for at least 6 months at 4° C. is obtained.

EXAMPLE 6

Preparation of a Vaccine Composition Against Influenza Virus from a DC chol/DOPE Liposomal Suspension 3 ml of a liposomal suspension obtained according to Example 4 are mixed with 0.2 ml of strain A/Singapore monovalent influenza vaccine containing the equivalent of 50 μg of the antigen consisting of the haemagglutinin HA.

The mixture obtained is then divided into 10 vaccine doses of 0.3 ml, each containing 5 μg of HA and 0.45 mg of DC chol.

EXAMPLE 7

Preparation of a Vaccine Composition Against Influenza Virus from a DC chol/DOPC Liposomal Suspension 3 ml of a liposomal suspension obtained according to Example 5 are mixed with 0.2 ml of strain A/Singapore monovalent influenza vaccine.

The mixture obtained is then divided into 10 vaccine doses of 0.3 ml, each containing 5 μg of HA and 0.45 mg of DC chol.

EXAMPLE 8

Immunization 5 groups of 4 Balb/c mice are immunized by 3 subcutaneous injections performed on D0, D21 and D36 with the following vaccine compositions:

Group A: 0.3 ml of diluted strain A/Singapore monovalent influenza vaccine containing 5 μg of HA in 0.3 ml of PBS, Group B: 0.3 ml of vaccine composition obtained according to Example 2, Group C: 0.3 ml of vaccine composition obtained according to Example 3, Group D: 0.3 ml of vaccine composition obtained according to Example 6, Group E: 0.3 ml of vaccine composition obtained according to Example 7.

EXAMPLE 9
Assay for Anti-HA Antibodies

In order to perform the assays for neutralizing antibodies, the sera of mice are sampled on D21, D36 and D5, and the titration of anti-HA antibodies is performed by means of the technique of inhibition of influenza virus-induced haemagglutination.

Figure 17:
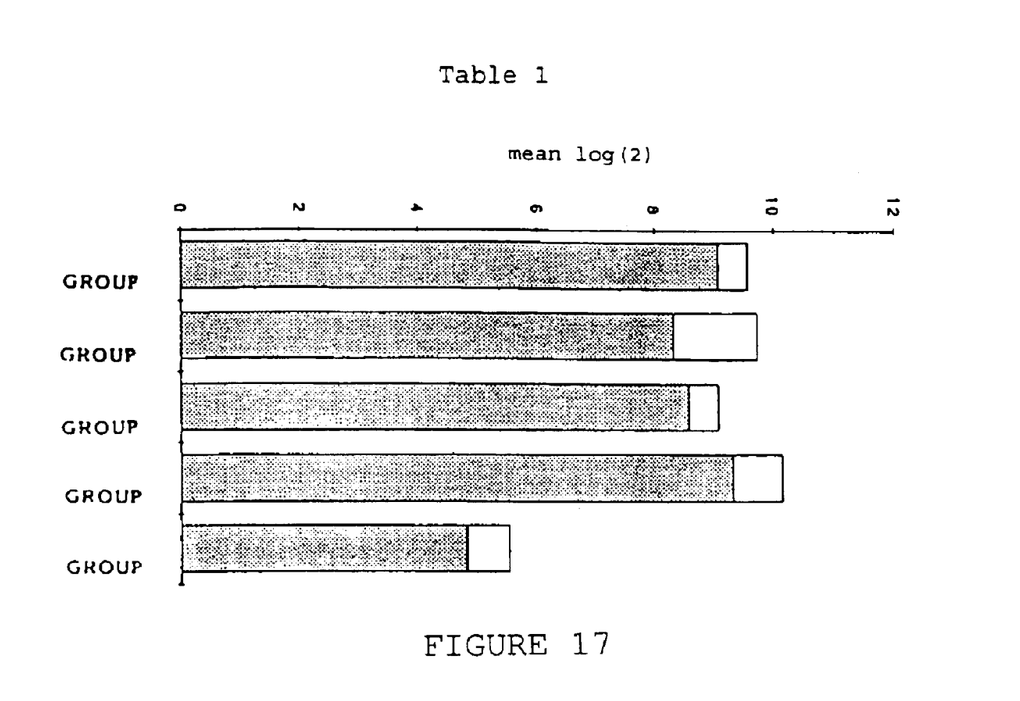
FIG. 17 depicts the results mention in Example 9.
Figure 18:
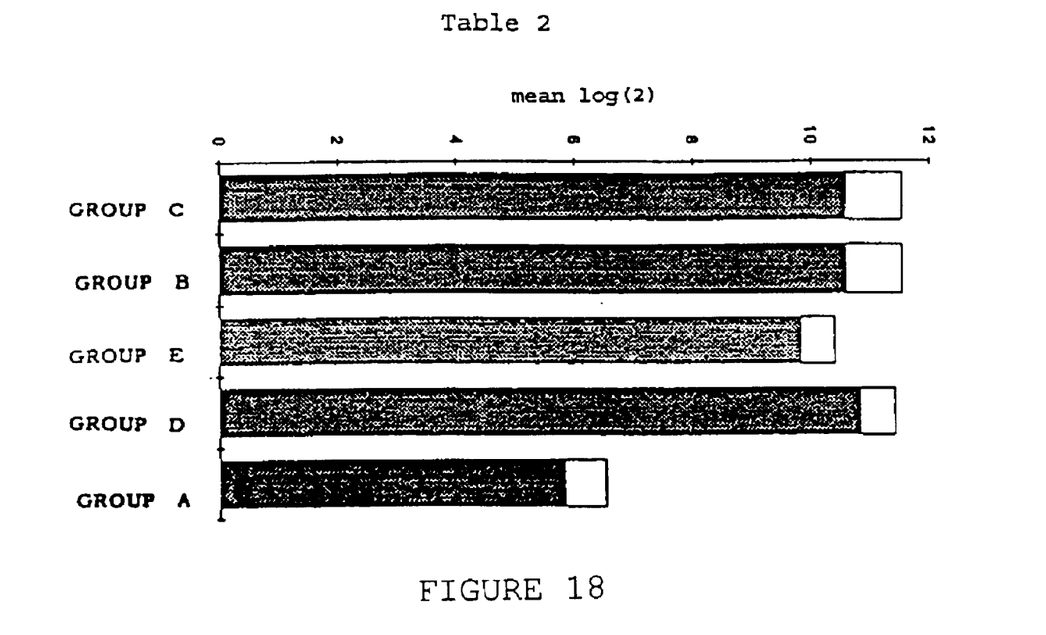
FIG. 18 depicts the results mention in Example 11.

FIG. 17 below illustrates the results obtained for each group of mice after one injection, and FIG. 18 the results after 2 injections.

The titres of neutralizing antibodies in the mouse sera are presented in the form of log2 of the highest dilution inducing haemagglutination inhibition.

These results show clearly the adjuvant role played by DC chol. In effect, the level of anti-HA antibodies is markedly higher for the groups of mice which have received DC chol in comparison with mice which have received the vaccine without adjuvant (Group A).

It is important to note that the levels of neutralizing antibodies in Groups B, C, D and E are greater than the level of neutralizing antibodies in Group A, even after a single injection of the different vaccine compositions. These titres increase slightly more and stabilize after the second injection. The results obtained after the 3rd injection are substantially equal to those for the 2nd injection (not shown).

Tests carried out with a trivalent influenza vaccine comprising strain A/Texas, strain B/Panama and strain A/Beijing also demonstrated the adjuvant power of DC chol.

EXAMPLE 10
Demonstration of the Induction of Cytotoxic T Cells

The spleen cells of the mice of each of the groups mentioned in Example 8 are removed on D51.

These effector cells are restimulated in vitro in the presence of syngeneic stimulatory cells infected with the strain A/Singapore virus corresponding to the vaccine tested. The specific cytotoxic function of these stimulated cells is demonstrated using as target cells the P815 mastocytoma line sensitized by incubation with a peptide which is a CTL epitope of the haemagglutinin of the virus (specific response against the HA) or with a peptide which is a CTL epitope of the nucleoprotein of the virus (specific response against the NP). Non-specific lysis (background) is measured on P815 cells which are unsensitized or sensitized with a peptide which is a CTL epitope of the HIV virus (V3MN).

Lysis of the target cells is measured by a radioactive technique based on loading of the target cells with Cr-51 and on release of this radioelement during cell lysis.

The results presented in FIGS. 2 to 6, which illustrate the percentage cytotoxicity in terms of the ratio of effector cells to target cells for each of the groups of mice tested, show that it is especially advantageous to use a liposomal composition of DC chol especially in combination with a neutral lipid, since this composition makes it possible to induce specific cytotoxic T lymphocytes in addition to the humoral type immune response obtained as a result of the adjuvant action of the DC chol.

EXAMPLE 11
Study of the Immune Response as a Function of the Dose of DC chol Used Vaccine compositions of 300 μl are prepared, each containing strain A/Singapore monovalent influenza vaccine and containing either 15 or 5 μg of HA, in combination with DC chol/DOPC liposomes at a variable concentration. The preparation of liposomal suspension is carried out in a manner similar to that of Example 4, replacing the 18 mg of dioleoylphosphatidylethanolamine (DOPE) by 13.5 mg of dioleoylphosphatidylcholine (DOPC) and taking up the lipid film obtained with an amount of water which varies according to the desired DC chol concentration.

The vaccine compositions obtained are injected into groups of 5 8- to 10-week-old female Balb/c mice on D0 and D28. The sera are sampled on D42 and the anti-HA antibodies are assayed by the agglutination inhibition (HAI) technique.

Figure 7:
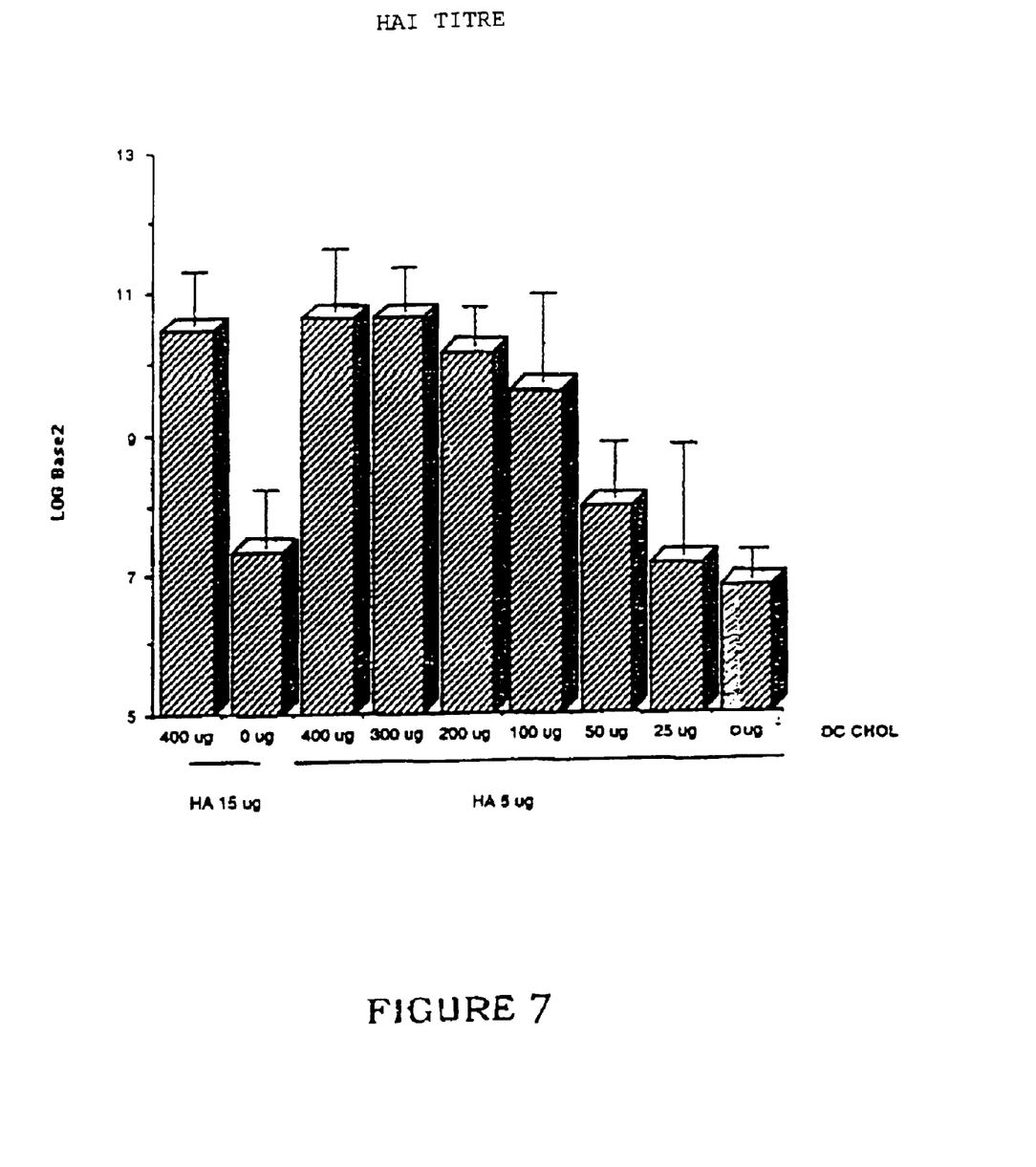
FIG. 7 depicts the results mentioned in Example 11.

The following compositions are tested in this way:
15 μg of HA+0 μg of DC chol
15 μg of HA+400 μg of DC chol
5 μg of HA+0 μg of DC chol
5 μg of HA+25 μg of DC chol
5 μg of HA+50 μg of DC chol
5 μg of HA+100 μg of DC chol
5 μg of HA+200 μg of DC chol
5 μg of HA+300 μg of DC chol
5 μg of HA+400 μg of DC chol The results expressed in the form of log base 2 of the highest dilution inducing haemagglutination inhibition are depicted in FIG. 7, and show that only above 100 μg of DC chol/dose is the maximum benefit of the adjuvant effect of DC chol obtained.

EXAMPLE 12
Demonstration of the Induction of Different Antibody Isotypes

A comparative study is carried out of the antibodies induced in 3 groups of 5 8- to 10-week-old female BALB/c adult mice which have received 2 subcutaneous injections performed on D0 and D28 with the following vaccine compositions:

1st group: 0.3 ml of diluted strain A/Singapore monovalent influenza vaccine containing 5 μg of HA in 0.3 ml of PBS, 2nd group: 0.3 ml of diluted strain A/Singapore monovalent influenza vaccine containing 5 μg of HA with 0.1 mg of aluminium hydroxide as adjuvant, 3rd group: 0.3 ml of vaccine composition obtained according to Example 11 and containing 5 μg of HA and 400 μg of DC chol in combination with DOPC.

The sera of the mice are sampled on D28 and on D42 and the IgG1 and IgG2 produced are assayed by the ELISA technique.

Figure 8:
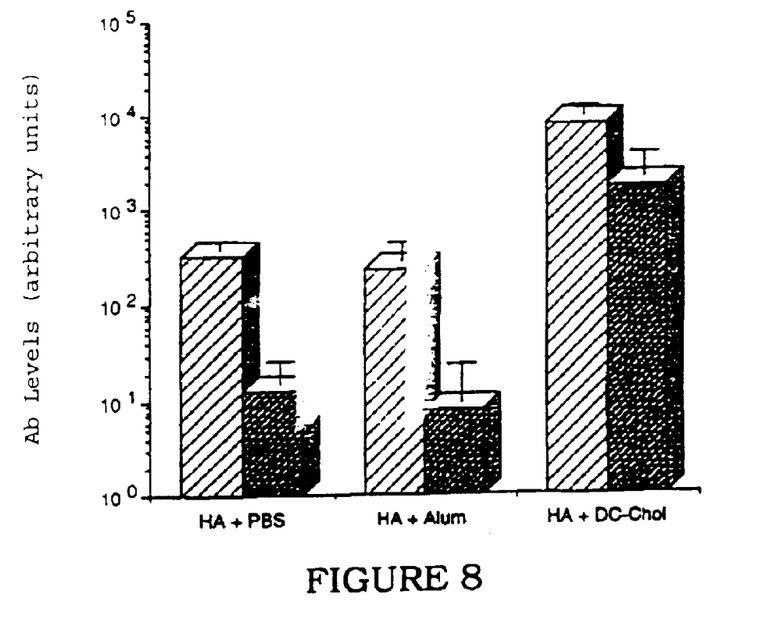
FIGS. 8 and 9 depict the results mentioned in Example 12.
Figure 9:
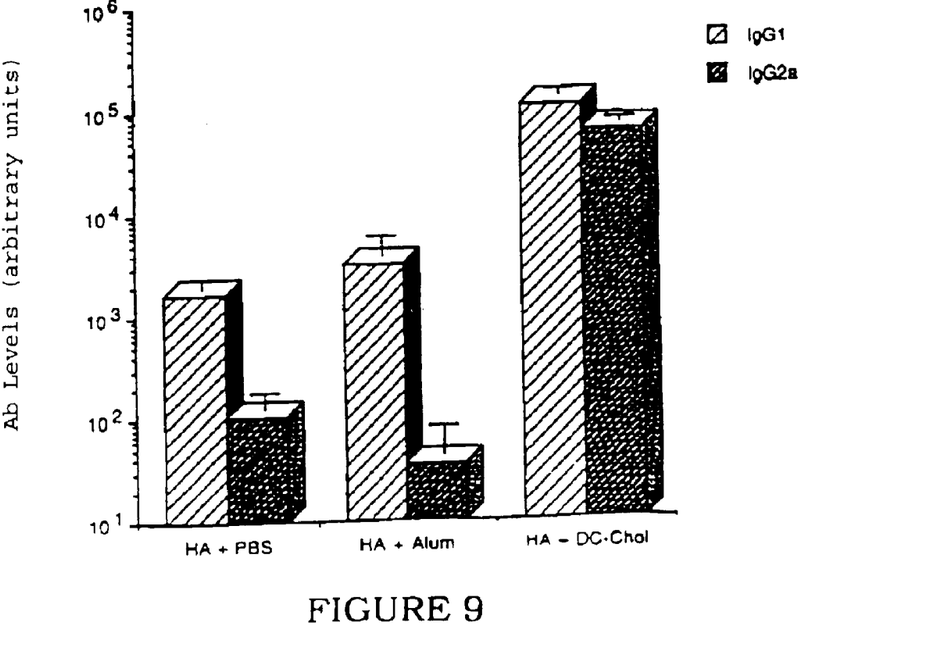

The results obtained in the primary response are depicted in FIG. 8 and those obtained in the secondary response are depicted in FIG. 9.

These results illustrate the adjuvant effect of DC chol, both in the primary response and in the secondary response, in comparison to aluminium hydroxide which is an adjuvant of the prior art. It will be noted, in addition, that there is a large increase in the IgG2a produced, signifying that DC chol acts by promoting the development of TH1 type lymphocytes.

EXAMPLE 13
Demonstration of the Action of DC chol in Elderly Mice

The same experiment is carried out exactly as in Example 12 but, in this instance, the mice tested are 20 to 22-month-old mice which are more difficult to stimulate.

Figure 10:
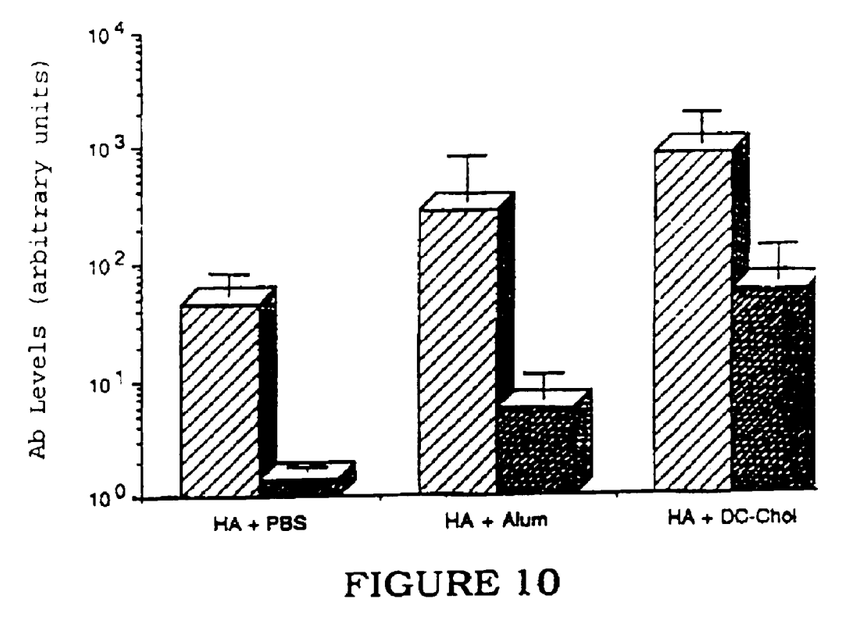
FIGS. 10 and 11 depict the results mentioned in Example 13.
Figure 11:
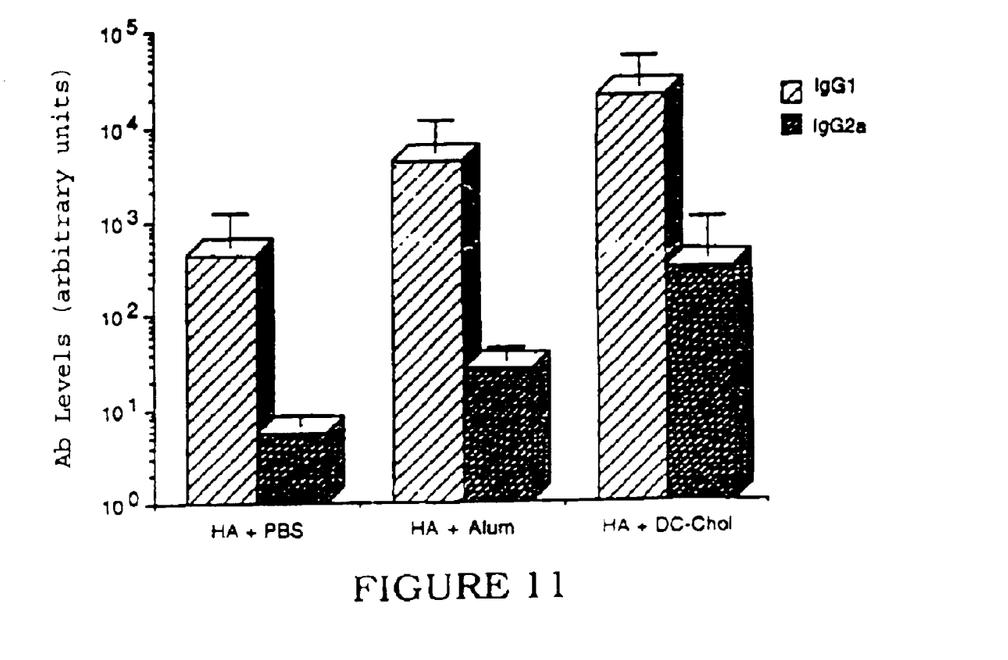

The results obtained in the primary response are depicted in FIG. 10 and those for the secondary response in FIG. 11.

Here too, DC chol has an adjuvant effect both for the primary response and for the secondary response, and in particular with respect to the induction of IgG2a antibodies.

EXAMPLE 14
HAI Levels in Adult Mice and in Elderly Mice

In the tests carried out in Examples 12 and 13, the neutralizing antibodies are determined in the immunized mice by the haemagglutination inhibition (HAI) test.

Figure 12:
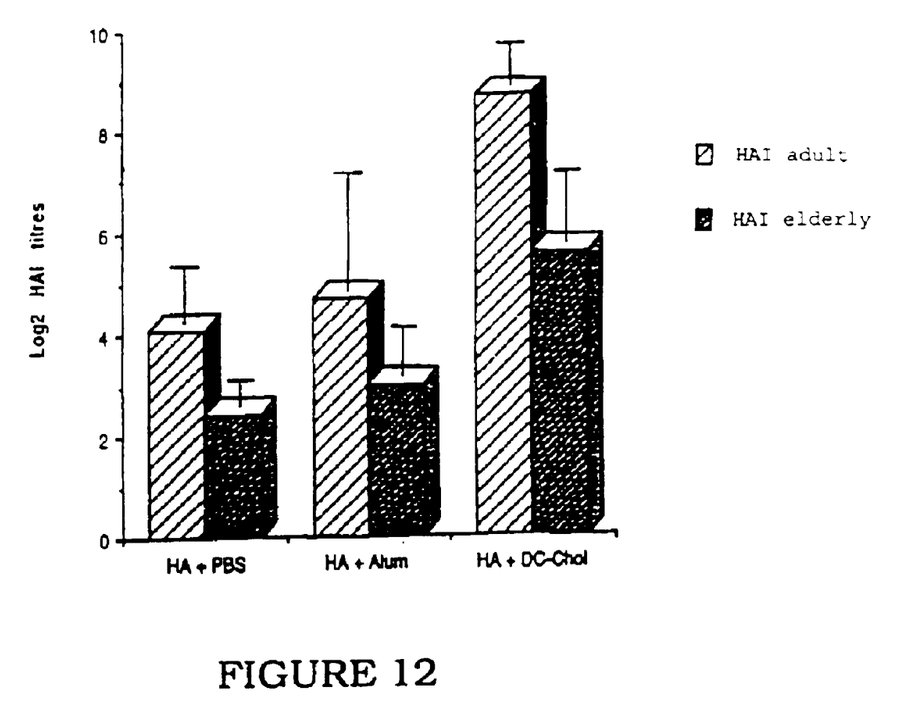
FIGS. 12 and 13 depict the results mentioned in Example 14.
Figure 13:
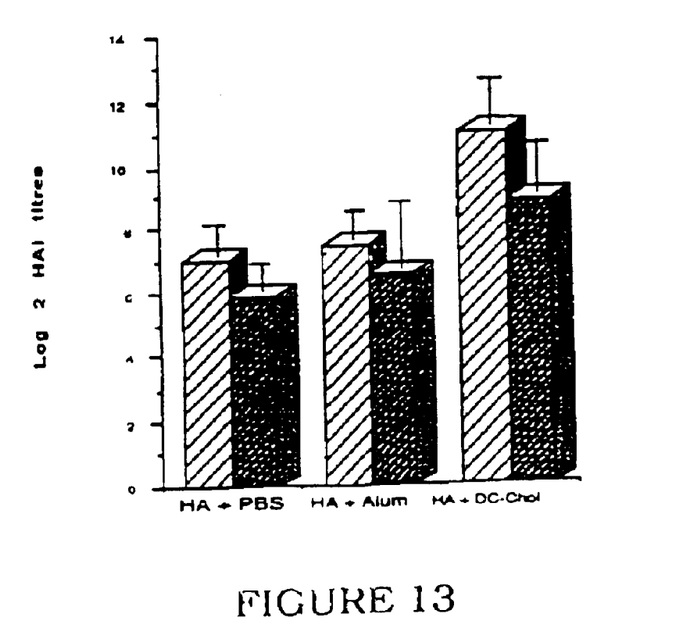

The results obtained in the primary response are illustrated in FIG. 12 and those for the secondary response in FIG. 13. The titres obtained, expressed in the form of log base 2 of the highest dilution inhibiting haemagglutination, shows clearly the adjuvant role of the DC chol/DOPC liposomes both in adult mice and in elderly mice.

EXAMPLE 15
Intranasal Immunization

Vaccine compositions are prepared as described in Example 11, in this instance of 50 µl comprising 5 µg of HA (in the form of strain A/Singapore monovalent influenza vaccine) combined with 200 µg of DC chol present in the form of DC chol/DOPC (in a mass ratio of 1 to 4) liposomes.

Two groups of 4 BALB/c mice are immunized intranasally twice with an interval of 4 weeks.

The 1st group of mice ($G_1$) receives 50 µl of the vaccine composition containing 200 µg of DC chol, whereas the second group ($G_2$) receives 50 µl of the same monovalent influenza vaccine but without adjuvant. The immune responses of each group are analysed by ELISA assay of the sera sampled 3 weeks after the booster immunization.

Figure 14:
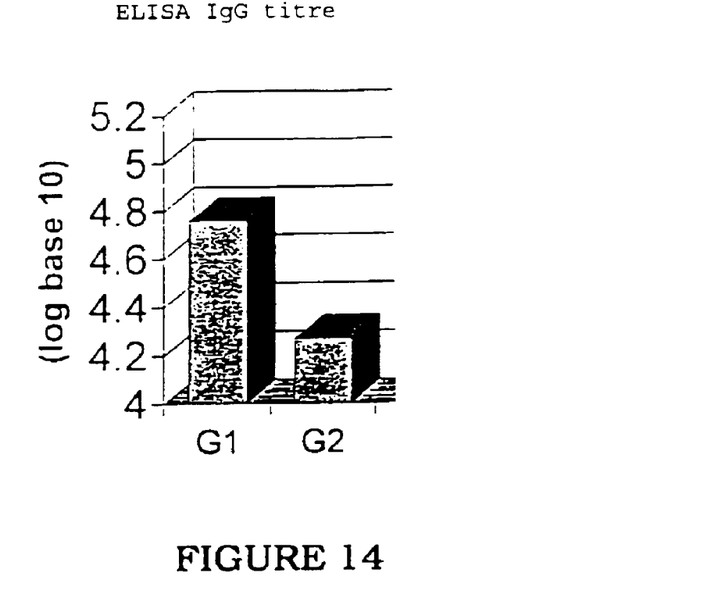
FIGS. 14 and 15 depict the results mentioned in Example 15.
Figure 15:
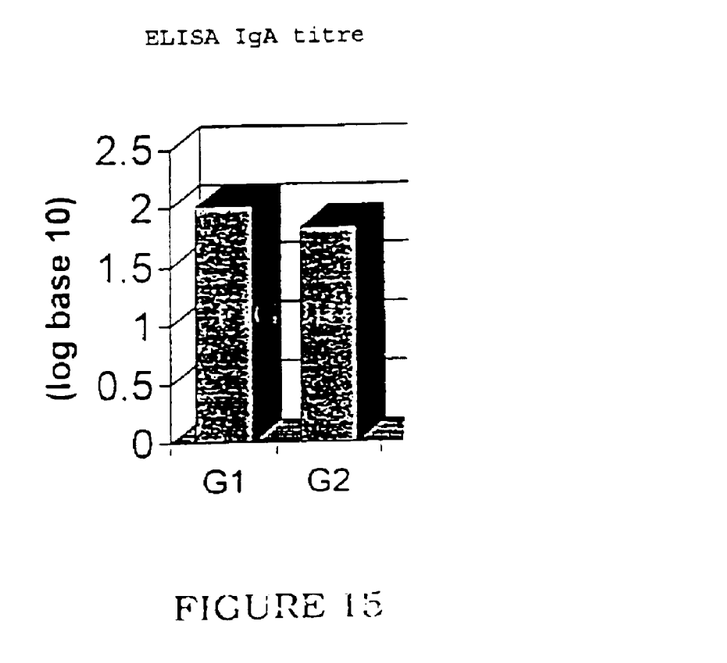

The results, expressed in the form of log base 10 of the ELISA titre, are depicted in FIG. 14 as regards the serum IgG and in FIG. 15 as regards the serum IgA.

It will thus be noted that, in a protocol of strict mucosal administration, the DC chol/DOPC liposomes enable the local and general immune responses to be increased by a factor of at least 2.

The adjuvant role performed by the DC chol/DOPC liposomes in the general immune responses was also observed when, instead of measuring the IgG and IgA titres by ELISA, the anti-HA antibody titres were measured by HAI; the increase in the local immune response was also observed in an ELISPOT count of the number of cells secreting IgG and the number of cells secreting IgA in the lungs of the immunized mice, and also in the determination of the ratio of the level of specific IgG (or of IgA) to the level of total IgG (or of IgA, respectively) measured by ELISA in the nasopharyngeal lavage fluids of the immunized mice.

EXAMPLE 16
Immunization by Combined Subcutaneous and Intranasal Administration Two groups of 4 BALB/c mice are immunized twice with an interval of 4 weeks with, on each occasion, the following vaccine compositions:

Group 3 ($G_3$):—a vaccine composition of 300 µl injected subcutaneously comprising 4 µg of HA (in the form of strain A/Singapore monovalent influenza vaccine) combined with 6 pg of DC chol (in the form of DC chol/DOPC liposomes), and     a vaccine composition of 50 µl administered intranasally comprising 0.25 µg of HA (in the form of strain A/Singapore monovalent influenza vaccine) combined with 6 µg of DC chol (in the form of DC chol/DOPC liposomes), Group 4 ($G_4$):—a vaccine composition of 300 µl injected subcutaneously comprising 4 µg of HA combined with 200 µg of DC chol, and     a vaccine composition of 50 µl administered intranasally comprising 0.25 µg of HA combined with 200 µg of DC chol.

The sera of the immunized mice are sampled 3 weeks after the booster administration and, for each mouse, the level of neutralizing antibodies is assayed by the HAI haemagglutination inhibition technique.

Figure 16:
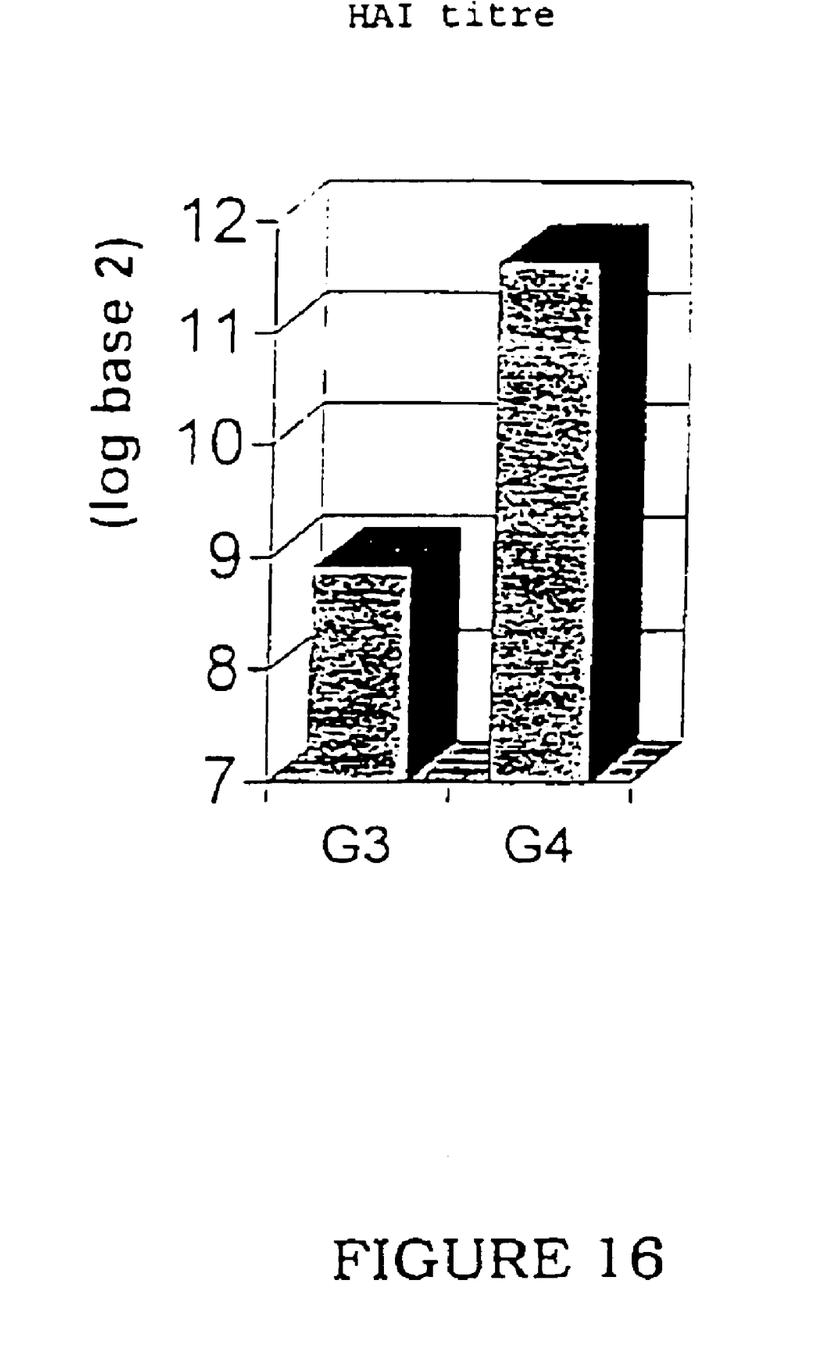
FIG. 16 depicts the results mentioned in Example 16.

The results obtained, expressed in the form of log base 2 of the titre, are depicted in FIG. 16, and show that, in a protocol of mixed administration combining the subcutaneous and intranasal routes, DC chol has an adjuvant effect, and that the increase in the dose of DC chol from 6 to 200 µg enables the immune response to be increased.

An identical dose effect could be observed when, instead of measuring the level of anti-HA antibodies by the HAI technique, the serum IgG was measured by the ELISA technique or the number of cells secreting IgG and the number of cells secreting IgA was measured in the lungs of the immunized mice (by the ELISPOT technique), or the ratio of the amounts of specific IgG (or IgA) to the amounts of total IgG (or IgA, respectively) was measured in the nasopharyngeal lavage fluids of the immunized mice.

Results similar to those described in Examples 11 to 16 were obtained by replacing DOPC by DOPE, as well as by varying the DC chol/neutral lipid ratio, maintaining the molar proportion of neutral lipid combined with DC chol at not less than 20%.

What is claimed is:

1. A vaccine composition comprising at least one antigen and an adjuvanting amount of 3-β-(N-(N'-N-'-dimethylaminoethane)carbamoyl) cholesterol.

2. The vaccine composition of claim 1, wherein said antigen is an influenza antigen.

3. The vaccine composition of claim 1, further comprising a neutral lipid.

4. The vaccine composition of claim 3, wherein the ratio of said neutral lipid to said 3-β-(N-(N'-N'-dimethylaminoethanelcarbamoyl) cholesterol is greater than 1:4.

5. The vaccine composition of claim 3, wherein said neutral lipid is dioleoylphosphatidylethanolamine or dioleoylphosphatidylcholine.

6. The vaccine composition of claim 1, wherein said 3-β-(N-(N'-N'-dimethylaminoethane)carbamoyl) cholesterol is dispersed in an aqueous environment in the form of liposomes.

7. The vaccine composition of claim 1, wherein said 3-β-(N-(N-N'-dimethylaminoethane)carbamoyl) cholesterol takes the form of liposomes including at least one antigen.

8. A method of inducing an immune response in a mammal, comprising administering the vaccine composition of claim 1, to a mammal.

9. The method of claim 8, wherein said immune response is a humoral immune response.

10. The method of claim 8, wherein said immune response is a cytotoxic T cell response.

11. The method of claim 8, wherein said immune response is a $TH_1$-type immune response.

12. The method of claim 11, wherein said antigen is an influenza virus haemagglutinin.

13. The method of claim 8, wherein said antigen is an influenza virus haemagglutinin.

14. The method of claim 8, wherein said vaccine composition is administered by the subcutaneous route.

15. The method of claim 8, wherein said vaccine composition is administered by the mucosal route.

16. The method of claim 8, wherein said vaccine composition is administered by the intranasal route.

17. A method of inducing an immune response in a mammal, comprising administering an immunogenic amount of the vaccine composition of claim 1 to a mammal.

18. The method of claim 17, wherein the antigen is an influenza virus haemagglutinin.

19. The method of claim 17, wherein said immune response is a humoral immune response.

20. The method of claim 17, wherein said immune response is a cytotoxic T cell response.

21. The method of claim 17, wherein said immune response is a $TH_1$-type immune response.

22. The method of claim 21, wherein said antigen is an influenza virus haemagglutinin.

23. The method of claim 17, wherein said composition is administered by the subcutaneous route.

24. The method of claim 17, wherein said composition is administered by the mucosal route.

25. The method of claim 17, wherein said composition is administered by the intranasal route.

* * * * *